US007037378B2

(12) United States Patent
Jumppanen et al.

(10) Patent No.: US 7,037,378 B2

(45) Date of Patent: May 2, 2006

(54) SEPARATION OF SUGARS

(75) Inventors: Juho Jumppanen, Redhill (GB); Vili Ravanko, Clinton, IA (US); Heikki Heikkilä, Espoo (FI); Juha Nurmi, Kirkkonummi (FI); Nina Nurmi, Helsinki (FI); Pia Saari, Espoo (FI); Katja Häkkä, Espoo (FI); Jari Lewandowski, Siuntio (FI)

(73) Assignee: Danisco Sweetners Oy, Kotka (FI)

( * ) Notice: Subject to any disclaimer, the term of this patent is extended or adjusted under 35 U.S.C. 154(b) by 16 days.

(21) Appl. No.: 10/670,094

(22) Filed: Sep. 24, 2003

(65) Prior Publication Data

US 2005/0061313 A1 Mar. 24, 2005

(51) Int. Cl.

| | |
|---|---|
| ***C07H 1/06*** | (2006.01) |
| ***C07H 1/08*** | (2006.01) |
| ***C07H 3/08*** | (2006.01) |
| ***C13K 1/00*** | (2006.01) |
| ***C13K 13/00*** | (2006.01) |

(52) U.S. Cl. ...................... 127/30; 127/46.2; 536/1.11; 536/123.12; 536/127; 536/128

(58) Field of Classification Search .................. 127/30, 127/46.2; 536/1.11, 123.12, 127, 128
See application file for complete search history.

(56) References Cited

U.S. PATENT DOCUMENTS

| | | | | |
|---|---|---|---|---|
| 3,240,775 A | | 3/1966 | Schweiger | |
| 4,758,283 A | * | 7/1988 | Takemura et al. | 127/36 |
| 4,772,334 A | | 9/1988 | Hatanaka et al. | |
| 6,663,717 B1 | * | 12/2003 | Antila et al. | 127/34 |

FOREIGN PATENT DOCUMENTS

| | | |
|---|---|---|
| EP | 102535 | 3/1984 |
| EP | 0 560 284 A1 | 9/1993 |
| JP | 63027496 | 2/1988 |
| JP | 61210013 | 9/1996 |
| JP | 11035591 A | 2/1999 |
| WO | WO 02/27039 | 4/2002 |
| WO | WO 03/080872 A1 | 10/2003 |

OTHER PUBLICATIONS

Merck Index, Twelfth Edition, (1996)* p. 725.

Petra T. Vanhooren and Erick J. Vandamme, "Review: L-fucose: occurrence physiological role, chemical, enzymatic and microbial synthesis", *J. Chem. Technol. Biotechnol.* 74:479-497 (1999)*, p. 483-484 and 495).

Rombouts, F.M., et al., "Feruloylated pectic substances from sugar-beet pulp", *Carbohydrate Research*, pp. 154, 177-187, (1986).

Derevitskaya, V.A. et al., "Use of anion-exchange chromatography for the separation of complex mixtures of oligosaccharides", *Dokl. Akad. Nauk. SSSR*, (1975)*, 223(5) 1137-9, 1 page.

Simatupang, M.H., "Ion-exchange chromatography of some neutral monosaccharides and uronic acids", *Journal of Chromatography*, 178(2), pp. 588-591 (1979).

Balaghova, D. et al., "Changes of the saccharide portion of maple wood in the course of prehydrolysis", *Vybrane Procesy Chem. Spracovani Dreva*, pp. 187-192 (1996).

Defaye, J., et al., "An efficient synthesis of L-fucose and L-(4-$^2$H) fucose", *Carbohydrate Research*, 126, 165-169 (1984).

Gesson, J.-P., et al. "A Short Synthesis of L-Fucose and Analogs from D-Mannose", *Tetrahedron Letters*, Vo. 33, No. 25, pp. 3637-3640 (1992).

Dejter-Juszunski, Marta, et al., "Synthesis of L-fucose", *Carbohydrate Research*, 28(1), pp. 144-146 (1973).

Kristen, H., et al., "Introduction of a new selective oxidation procedure into carbohydrate chemistry. An efficient conversion of D-galactose into L-fucose", J. Carbohydr. Chem. 7(1), pp. 277-281 (1988).

Sabrajna, Sumita, et al., "A novel synthesis of L-fucose from D-galactose", *Carbohydr. Res.*, pp. 270, 93-96 (1965).

Wong, C., et al., "Enzymatic Synthesis of L-Fructose and Analogs" J. Org. Chem., 60:7360-7363 (1995).

* cited by examiner

*Primary Examiner*—David Brunsman
(74) *Attorney, Agent, or Firm*—Scully, Scott, Murphy & Presser

(57) ABSTRACT

The invention relates to the recovery of deoxy sugars, such as fucose from biomass-derived solutions, such as spent liquors obtained from pulping processes. The invention is based on the use of chromatographic fractionation with specific column packing materials and combinations thereof. The deoxy sugar product obtained from the chromatographic fractionation may be further purified by crystallization. The invention also provides a novel crystalline fucose product and a novel process for the crystallization of fucose.

48 Claims, 6 Drawing Sheets

SEPARATION OF SUGARS

FIELD OF THE INVENTION

The invention relates to the field of sugar separation technology. Especially, the invention relates to a process of separating deoxy sugars, such as fucose and particularly L-fucose from a solution containing the same. The invention also relates to a novel crystalline fucose product and a process for the crystallization of fucose.

BACKGROUND OF THE INVENTION

Deoxy sugars are examples of so-called rare sugars, which are found in small amounts in plant-based materials, such as wood resources, seaweeds and sugar beet and sugar cane. Specific deoxy sugars have been found useful for example for sweetener applications as well as for pharmaceutical and cosmetic applications.

Deoxy sugars are known to exist in L-form and in D-form. For example, fucose exists as L-fucose and D-fucose.

One example of deoxy sugars of special interest is fucose, also named 6-deoxygalactose. Fucose is found in a wide variety of natural products from many different sources, in both D-form and L-form. Interest in L-fucose has recently increased because of its potential in the medical field in treating various disease conditions, such as tumors, inflammatory conditions and disorders relating to the human immune system. L-fucose has also applications in the cosmetic field, for instance as a skin moisturizing agent.

In accordance with Merck Index, Twelfth Edition, 1996, crystalline L-fucose has a melting point of 140° C. and an optical rotation of −75.6°.

L-fucose occurs for instance in several human milk oligosaccharides.

In plant material, fucose is typically associated with plant polysaccharides, which are often highly branched structures having L-fucopyranosyl units either at the ends of or within the polysaccharide chains. In some cases, even methylated fucopyranosyl units occur in plant polysaccharides.

L-fucose or methylated L-fucopyranosyl units occur in the cell walls of potato, cassava tuber and kiwi fruit, in the seed polysaccharides of soybean and in winged bean varieties and canola, for example.

Seaweed polysaccharides, found in the intercellular mucilage, form complex structures and are often composed of sulfated L-fucose polymers, named fucoidan. Seaweeds of particular importance for the extraction of fucoidan are *Ecklonia kurome, Laminaria angustata* var *longissima, Fucus vesiculosus, Kjellmaniella crassifolia, Pelvetia canaliculata* and *Fucus serratus* L.

Furthermore, extracellular polysaccharides from various bacteria, fungi and micro-algae contain L-fucose.

L-fucose can be obtained from natural sources, such as algae by various extraction methods. These raw materials of natural origin used for the recovery of fucose are typically multicomponent mixtures. The separation of fucose with sufficient purity has presented a problem in the state of the art.

L-fucose has been obtained by hydrolysis of fucoidan occurring in *Phaeophyceae* algae. Black, W. A. P. et al. disclose an optimized fucoidan extraction method in "Manufacture of algal chemicals. IV. Laboratory-scale isolation of fucoidan from brown marine algae", J. Sci. Food Agric. 3:122–129 (1952). The highest yields were obtained by extraction (pH 2.0–2.5) with hydrochloric acid at a temperature of 70° C. for 1 h. A ratio (w/v) of 1 unit algae to 10 units liquid was shown to be optimal. This procedure yielded about 50% of the total L-fucose. Three subsequently performed acid extractions yielded more than 80% L-fucose. The crude fucoidan was isolated from the acid extraction liquid by neutralization and evaporation to dryness.

U.S. Pat. No. 3,240,775, Kelco Co. (published 15 Mar. 1966) discloses a method of preparing crystals of an α-L-fucoside and L-fucose comprising the steps of heating a mixture of fucoidan, concentrated hydrogen chloride and methanol until the fucoidan is substantially depolymerized and desulfated, and thereafter recovering, from said mixture, a degradation product which consists of methyl α-L-fucoside and, after subsequent hydrolysis, L-fucose.

Example VIII of the above-mentioned reference discloses a process of obtaining crystalline L-fucose from said mixture containing fucoidan degradation products by removing the α-L-fucoside (methyl α-L-fucoside), treating the mixture thus obtained with 1 N sulfuric acid, precipitating sulfuric acid with $Ba(OH)_2$, treating the solution with cation exchange resins (Amberlite IR-120 in $H^+$ form) and activated carbon, concentrating the colorless solution in vacuo to a syrup and diluting the syrup with hot methanol. Ether was added to the diluted solution, and after seeding with L-fucose the mixture was kept refrigerated for 8 to 12 days. Crystalline L-fucose with a melting point of 136 to 138° C. was obtained. In accordance with Example IX, the same procedure provided crystalline L-fucose with a melting point of 136 to 139° C.

Japanese patent publication 63027496 A2 (Takemura, M et al., Towa Chem. Ind.) describes direct extraction of L-fucose from algae belonging to the family of the *Chordariaceae* or *Spermatochnaceae*. The algae were dispersed in water and treated with concentrated sulfuric acid. The obtained hydrolyzate was cooled and the algae residues were removed by filtration. The pH of the filtrate was adjusted to 5, the filtrate was treated with charcoal and filtered. A yeast was added to the filtrate to digest the saccharides other than L-fucose. The mixture was treated with charcoal and filtered. The filtrate was subjected to deionization treatment with cation and anion exchange resins and concentrated. The concentrated sugar solution was mixed with ethanol and allowed to crystallize. In this way, L-fucose with a purity of 98.7% was obtained. Melting point data for the L-fucose product was not given.

F. M. Rombouts and J. F. Thibault describe the isolation of pectins from an ethanol-insoluble residue of sugar beet pulp in Carbohydrate Research 1986, 154, pp. 177–187. The isolated pectins were purified by chromatography on DEAE-cellulose or by precipitation with $CuSO_4$. The pectins had relatively high contents of neutral sugars. The main neutral sugars in each pectin were arabinose and galactose; other sugars present were rhamnose, fucose, xylose, mannose and glucose. Fucose was not separated from the sugar/pectin mixture.

V. A. Derevitskaya et al. (Dokl. Akad. Nauk. SSSR (1975), 223(5) 1137–9) describe the separation of complex mixtures of oligosaccharides by anion-exchange chromatography. In accordance with the disclosure, 2-amino-2-deoxy-glucitol, glucosamine, galactose and fucose were successfully separated from oligosaccharide mixtures, buffered by 0.2 M borate, by anion-exchange chromatography.

M. H. Simatupang describes ion-exchange chromatography of some neutral monosaccharides and uronic acids in J. Chromatogr. (1979), 178(2), 588–91. The reference discloses ion-exchange chromatography of complex mixtures of uronic acids and monosaccharides containing fucose and mannuronic and guluronic acids utilizing a borate buffer system. The chromatographic system employed a steel column containing HA-X4 or BA-X4 (borate form) anion exchangers and a buffer system of various borate concentrations at various pH values.

D. Balaghova et al. studied the changes of the saccharide portion of maple wood in the course of prehydrolysis in Vybrane Procesy Chem. Spracovani Dreva (1996), 187–192 (Publisher: Technicka Univerzita Zvolen, Zvolen, Slovakia). The main monosaccharides found in maple wood were D-glucose, D-xylose, L-rhamnose, L-fucose, L-arabinose, D-mannose and D-galactose. L-fucose was not separated from the sugar mixture.

L-fucose can also be obtained via chemical synthesis from L-arabinose (Tanimura, A., Synthesis of L-fucose, Chem. Abstr. 55:12306 (1961)), from D-glucose (Chiba, T. & Tejima, S., A new synthesis of α-L-fucose, Chem. Pharm. Bull. 27:2838–2840 (1979)), from methyl-L-rhamnose (Defaye, J., et al., An efficient Synthesis of L-fucose and L-(4-$^{2}$H)fucose, Carbohydrate Res. 126:165–169 (1984)), from D-mannose (Gesson, J-P et al., A short synthesis of L-fucose and analogs from D-mannose, Tetrahedron Lett. 33:3637–3640 (1992)) and from D-galactose (Dejter-Juszynski, M & Flowers, H-M., Synthesis of L-fucose, Carbohydrate Res. 28:144–146 (1973); Kristen, H., et al., Introduction of a new selective oxidation procedure into carbohydrate chemistry—An efficient conversion of D-galactose into L-fucose, J. Carbohydr. Chem. 7:277–281(1988); Sarbajna, S. et al., A novel synthesis of L-fucose from D-galactose, Carbohydr. Res. 270:93–96 (1965)).

Enzymatic and microbial synthesis has also been used for the production of L-fucose.

C. Wong et al. disclose an enzymatic synthesis of L-fucose and analogs thereof in J. Org. Chem., 60:7360–7363 (1995). L-fucose is produced by enzymatic synthesis from dihydroxyacetone phosphate (DHAP) and DL-lactaldehyde catalyzed by L-fuculose-1-phosphate aldolase, followed by reaction with acid phosphatase and L-fucose isomerase. The L-fucose product was isolated by Dowex 50W-X8 ($Ba^{2+}$ form) chromatography, optionally combined with separation by silica gel.

EP 102 535, Hoecst AG (published 14 Mar. 1984) discloses a process for the production of deoxysugars selected from fucose and rhamnose by fermentation using the genera *Alcaligenes, Klebsiella, Pseudomonas* or *Enterobacter*, which produce extracellular polysaccharides containing more than 10% fucose and/or rhamnose. It is recited that fucose and/or rhamnose are recovered from the hydrolyzate of the fermentation product by chromatography, ion-exchange or adsorption (for example with zeolites) or by further fermentation treatment. In the examples of the EP patent, rhamnose and fucose are recovered by further fermentation treatment.

U.S. Pat. No. 4,772,334. Kureha Kagaku Kogyo Kabushiki Kaisha (published Sep. 20, 1988) discloses a process for producing highly pure rhamnose from gum arabic. The process comprises partial hydrolysis of gum arabic in an aqueous solution of a mineral acid, neutralization and treatment with a polar organic solvent to obtain an aqueous solution containing monosaccharides formed by the hydrolysis of gum arabic, and subjecting the aqueous solution thus obtained to strongly acid cation exchange chromatography and then to a method of adsorption and separation using activated carbon.

WO 02/27039, Xyrofin Oy (published 4 Apr. 2002) discloses a process for recovering a monosaccharide selected from the group consisting of rhamnose, arabinose and mixtures thereof from a solution containing the same by a multistep process comprising at least one step where a weakly acid cation exchange resin is used for the chromatographic separation.

One of the problems associated with known processes is that they provide the desired deoxy sugars as a mixture with other closely related sugars or that they do not provide the deoxy sugars, such as fucose with a sufficient degree of purity. Direct extraction from brown algae is costly, and subject to seasonal variations in the supply volume and quality. On the other hand, the production of L-fucose via chemical synthesis for instance from other sugars may be costly and suffer from low yield. Furthermore, it has been problematical to prepare suitable starting fucose solutions for the crystallization of fucose to obtain a crystalline fucose product having a purity of more than 99%.

Furthermore, the recovery of deoxy sugars from one another has presented a problem in the state of the art due to the closely related structures thereof. In many separation processes, the deoxy sugars behave in the same way, whereby no essential separation between these closely-related sugars occurs. Instead, they are often recovered as an admixture in the same fraction.

It has now been found that fucose and other deoxy sugars with high purity can be effectively recovered from biomass-derived solutions containing deoxy sugars and for example aldose and pentose sugars using a novel chromatographic separation method. It was also found that high purity fucose crystals with a melting point higher than 141° C., preferably higher than 145° C., can be obtained from impure syrups having a fucose content of more than 45% of DS, especially when the content of critical impurities is within a range below specific critical values. Fucose proved to have a very strong salting-out effect on other sugars, such as arabinose and rhamnose. For this reason, it has been very difficult to prepare fucose crystals with a high purity in the state of the art.

BRIEF DESCRIPTIONS OF THE INVENTION

An object of the present invention is to provide a method for recovering deoxy sugars, such as fucose from solutions containing the same. With the process of the invention, the disadvantages relating to the known processes can be alleviated. The objects of the invention are achieved by a process which is characterized by what is stated in the independent claims. The preferred embodiments of the invention are disclosed in the dependent claims.

The invention provides a versatile process of recovering one or more deoxy sugars from biomass-derived material. The biomass-derived material useful in the present invention may be for example a hemicellulose hydrolyzate containing deoxy sugars and for example aldose and pentose sugars from the hemicellulose. In a hemicellulose hydrolyzate derived for example from birch wood, fucose and rhamnose exist in L-form. The process of the invention is based on the use of one or more chromatographic fractionations with a column packing material selected from strongly acid cation exchange resins, weakly acid cation exchange resins, strongly basic anion exchange resins and weakly basic anion exchange resins. After the chromatographic separation, the fraction enriched in the desired deoxy sugar may be further crystallized to obtain the desired deoxy sugar with high purity.

With the chromatographic method of the invention, for example a fucose fraction having a purity between 10 and 90%, typically 40 to 80% or more can be obtained. The fucose fraction obtained from the chromatographic separation can be further purified by crystallization. The crystallization provides a fucose product having a purity of up to 99% or more and a melting point of 142.5° C. or higher. In a typical embodiment of the invention, the crystallization of fucose is carried out from a solution including as impurities less than 20% rhamnose, less than 15% xylose, less than 3% arabinose and less than 1% galactose on DS.

The process of the present invention thus provides the advantage that the desired deoxy sugars, such as fucose can be obtained with sufficient purity for medical applications, for example.

DEFINITIONS RELATING TO THE INVENTION

In the specification and throughout the examples and the claims, the following definitions are used:

"Deoxy sugar" refers to a monosaccharide derivative formed by the deoxidation of a hydroxyl group of the monosaccharide into an aldose or ketose form. Typical examples of deoxy sugars in connection with the present invention are rhamnose, fucose and methyl-α-D-xylose (MAX).

MAX refers to methyl-α-D-xylose.

SAC refers to a strongly acid cation exchange resin.

WAC refers to a weakly acid cation exchange resin.

SBA refers to a strongly basic anion exchange resin.

WBA refers to a weakly basic anion exchange resin.

DVB refers to divinylbenzene.

ACN refers to acetonitrile.

DS refers to a dry substance content measured by Karl Fischer titration, expressed as % by weight.

RDS refers to a refractometric dry substance content, expressed as % by weight.

Purity refers to the content of the compound expressed as % on dry substance.

SMB refers to simulated moving bed process.

BRIEF DESCRIPTION OF THE DRAWINGS

The following drawings are illustrative embodiments of the invention and are not meant to limit the scope of the invention in any way.

DETAILED DESCRIPTION OF THE INVENTION

Figure 1:
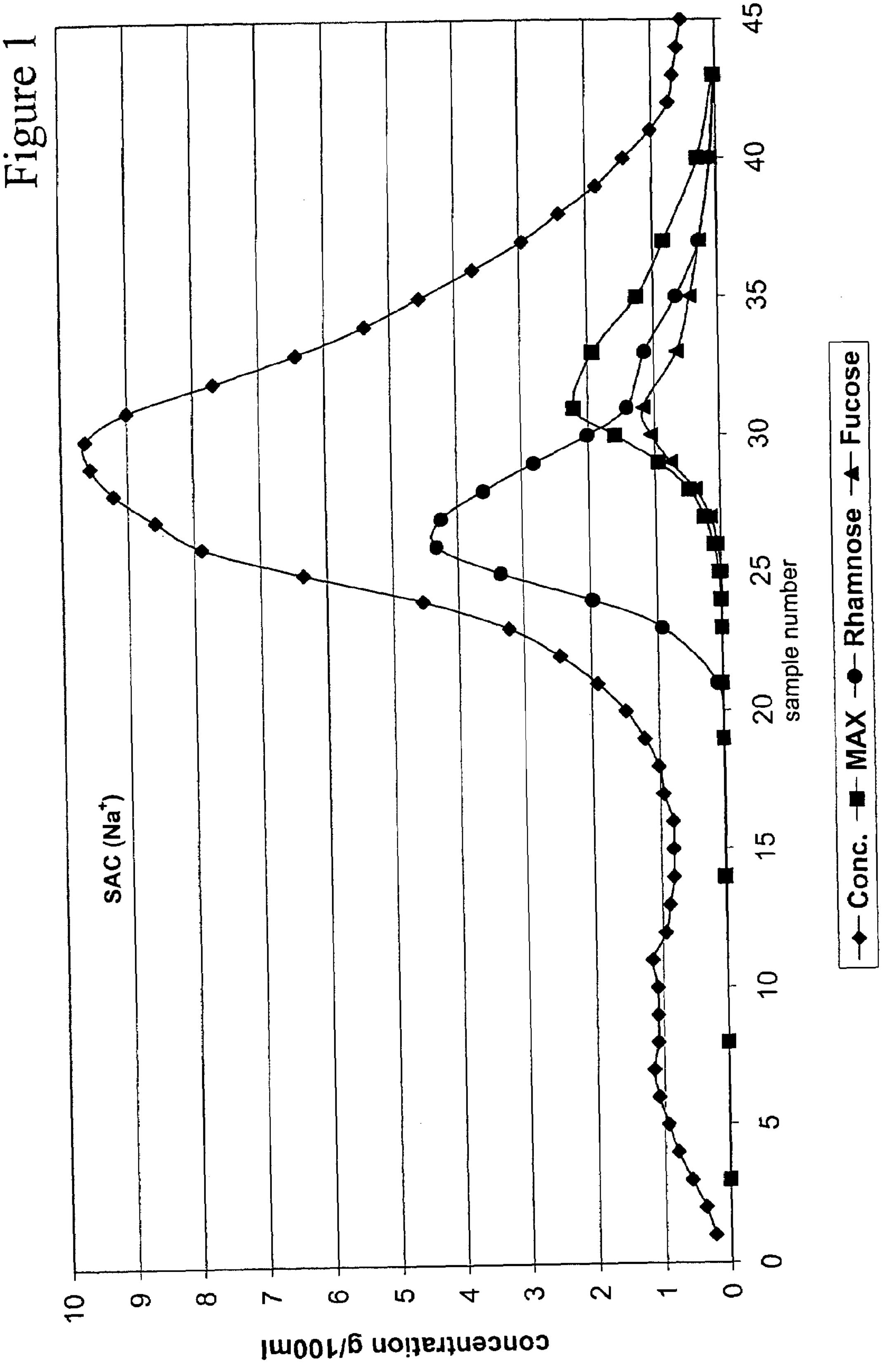
FIG. 1 is a graphical presentation of the separation profile obtained from Example 1 (chromatographic fractionation of a solution containing deoxy sugars using a strongly acid cation exchange resin in $Na^+$ form).

The present invention relates to a process of recovering one or more deoxy sugars from a solution derived from biomass containing deoxy sugars and ordinary sugars, such as pentose and hexose sugars. The process of the invention is characterized by subjecting the solution derived from biomass and containing deoxy sugars to one or more of steps (1), (2) and (3):

(1) at least one chromatographic fractionation using a column packing material selected from strongly acid cation exchange resins, (2) at least one chromatographic fractionation using a column packing material selected from weakly acid cation exchange resins and weakly basic anion exchange resins, (3) at least one chromatographic fractionation using a column packing material selected from strongly basic anion exchange resins, and recovering from steps (1), (2) and/or (3) one or more fractions enriched in at least one deoxy sugar.

In one embodiment of the invention, the process of the invention comprises subjecting said solution to two or more of steps (1), (2) and/or (3).

In another embodiment of the invention, the process of the invention comprises subjecting said solution to two or more times to steps selected from steps (1), (2) and/or (3).

In a further embodiment of the process of the invention, the process comprises recovering a fraction enriched in rhamnose from step (1).

In a still further embodiment of the process of the invention, the process comprises recovering a fraction enriched in methyl-α-D-xylose from step (2).

In a still further embodiment of the process of the invention, the process comprises recovering a fraction enriched in fucose from step (3).

In a further embodiment of the process of the invention, the process comprises step (3), i.e. subjecting said solution derived from biomass to chromatographic fractionation using a column packing material selected from strongly basic anion exchange resins and recovering a fraction enriched in fucose.

In step (2) of the process of the invention, the use of a weakly basic anion exchange resin typically provides the same separation result as a weakly acid cation exchange resin. Weakly basic anion exchange resins useful in the present invention are disclosed in a non-published Finnish Patent Application No. 20020592.

In a still further embodiment of the process of the invention, the process comprises the following sequential steps:

(1) subjecting said solution derived from biomass to chromatographic fractionation using a column packing material selected from strongly acid cation exchange resins and recovering a fraction enriched in rhamnose and/or one or more fractions containing deoxy sugars selected from methyl-α-D-xylose and fucose, (2) subjecting said one or more fractions containing methyl-α-D-xylose and fucose to chromatographic fractionation using a column packing material selected from weakly acid cation exchange resins and recovering a fraction enriched in methyl-α-D-xylose and a fraction containing fucose, (3) subjecting said fraction containing fucose to chromatographic fractionation using a column packing material selected from strongly basic anion exchange resins and recovering a fraction enriched in fucose.

In one embodiment of the invention, the invention also relates to a process with the following separation sequence: WAC(1)+WAC(2)+SAC(3), WAC(1) for the recovery of aldose sugars, WAC(2) for the recovery of MAX and SAC(3) for the recovery of rhamnose and fucose.

In another embodiment of the invention, the invention also relates to a process with the following separation sequence: WAC(1)+SAC(2)+WAC(3), WAC(1) for the recovery of aldose sugars, SAC(2) for the recovery of rhamnose and WAC(3) for the recovery of MAX and fucose.

In a further embodiment of the invention, the invention also relates to a process with the following separation sequence: WAC(1)+SBA(2), WAC(1) for the recovery of aldose sugars and SBA(2) for the recovery of MAX, rhamnose and fucose.

Said strongly acid cation exchange resins used as the column packing material in step (1) of the process of the invention may be in a monovalent cation form or in a divalent cation form. In a preferred embodiment of the invention, said strongly acid cation exchange resin is in $Na^+$ form. The resin may also be in $H^+$, $Mg^{2+}$ or $Ca^{2+}$ or $Zn^{2+}$ form, for example.

Said strongly acid cation exchange resin may have a styrene or acrylic skeleton. In a preferred embodiment of the invention, the resin is a sulphonated polystyrene-co-divinylbenzene resin. Other alkenylaromatic polymer resins, such as those based on monomers like alkyl-substituted styrene or mixtures thereof can also be applied. The resin may also be crosslinked with other suitable aromatic crosslinking monomers, such as divinyltoluene, divinylxylene, divinylnaphtalene, divinylbenzene, or with aliphatic crosslinking monomers, such as isoprene, ethylene glycol diacrylate, ethylene glycol dimethacrylate, N,N'-methylene bis-acrylamide or mixtures thereof. The crosslinking degree of the resin is typically from about 1 to about 20%, preferably from about 3 to about 8% of the crosslinking agent, such as divinylbenzene. The average particle size of the resin is normally 10 to 2000 μm, preferably 100 to 400 μm.

Said weakly acid cation exchange resins used as the column packing material in step (2) of the process of the invention may be in a monovalent or divalent cation form, preferably in $Na^+$ form. The resin may also be in $H^+$, $Mg^{2+}$ or $Ca^{2+}$ form, for example.

The weakly acid cation exchange resin is preferably an acrylic cation exchange resin having carboxylic functional groups. However, the resin may be other than an acrylic resin, for example a styrene resin, and the functional groups may be other than a carboxylic group, e.g. another weak acid. Such an acrylic resin is preferably derived from methyl acrylate, ethyl acrylate, butyl acrylate, methylmethacrylate or acrylonitrile or acrylic acids or mixtures thereof. The resin may be crosslinked with a crosslinking agent, e.g. divinylbenzene, or with the other crosslinking agents mentioned above. A suitable crosslinking degree is 1 to 20% by weight, preferably 3 to 8% by weight. The average particle size of the resin is normally 10 to 2000 μm, preferably 100 to 400 μm.

Said weakly basic anion exchange resin, which can alternatively be used in step (2) of the present invention, are preferably weakly basic anion exchange resins having an acrylic skeleton. The weakly basic anion exchange resin is preferably derived from acrylic esters ($H_2{=}CR{-}COOR'$, where R is H or $CH_3$ and R' is an alkyl group, such as methyl, ethyl, isopropyl, butyl etc.), such as methyl acrylate, ethyl acrylate, butyl acrylate, methyl methacrylate, acrylonitrile or acrylic acids or a mixture thereof. The acrylic matrix is crosslinked with a suitable crosslinker, which can be for example of aromatic type, such as divinylbenzene (DVB) or of aliphatic type, such as isoprene, 1,7-octadiene, trivinylcyclohexane, diethylene glycol divinyl ether, N,N'-methylenebisacrylamide, N,N'-alkylene bisacrylamides, ethylene glycol dimethacrylate and other di-, tri-, tetra-, pentacrylates and pentamethacrylates. A suitable crosslinking degree with divinylbenzene is from 1 to 10 weight-% DVB, preferably from 3 to 8 weight-%. The weakly basic anion resin is manufactured of the crosslinked polyacrylic polymer by amination with a suitable amine, such as mono-, di-, tri-, tetra-, penta- or hexamines or other polyamines. For example dimethylamine, diethylene triamine, triethylene tetramine, tetraethylene pentamine, pentaethylene hexamine and dimethylaminopropylamine are suitable amines.

Another weakly basic anion exchange resin structure is epichlorohydrin-based polycondensation anion exchangers. The chloromethyl and epoxy groups of epichlorohydrin react with polyamines forming crosslinked gel type anion exchangers. For example a condensation reaction of epichlorohydrin with triethylenetetramine results in the following anion resin structure. This type of anion resin contains both weakly basic (tertiary amine) and strongly basic (quaternary ammonium) functional groups.

Another class of weakly basic anion exchange resins is the aminated polycondensation products of phenol and formaldehyde.

Another well known way to produce weakly basic anion exchange resins are the aliphatic amines and ammonia polycondensation resins. Crosslinked resin structures are formed when monomeric amines or ammonia are reacted for example with formaldehyde. The reaction between amine and formaldehyde forms methylol and/or azomethine groups, which can further react to form polycondensates. A well-known structure of this type is a reaction resin of formaldehyde, acetone and tetraethylenepentamine. Aromatic amines can also be crosslinked with formaldehyde resulting in a weakly basic anion exchanger.

Different types of crosslinked polyvinylpyridine based ion exchangers having pyridine as the functional group are also useful as weakly base anion exchangers.

The average particle size of the resin is normally 10 to 2000 micrometers, preferably 100 to 400 micrometers.

Said strongly basic anion exchange resins used as the column packing materials in step (3) of the process of the invention are typically in $HSO_3^-$ form. Said strongly basic anion exchange resin may have a styrene or acrylic skeleton. The resin may be crosslinked with divinylbenzene. Other alkenylaromatic polymer resins, such as those based on monomers like alkyl-substituted styrene or mixtures thereof, can also be applied. The resin may also be crosslinked with other suitable aromatic crosslinking monomers, such as divinyltoluene, divinylxylene, divinylnaphtalene, divinylbenzene, or with aliphatic crosslinking monomers, such as isoprene, ethylene glycol diacrylate, ethylene glycol dimethacrylate, N,N'-methylene bis-acrylamide or mixtures thereof. The cross-linking degree of the resins is typically from about 1 to about 20%, preferably from about 3 to about 8% of the cross-linking agent, such as divinyl benzene. The average particle size of the resin is normally 10 to 2000 μm, preferably 100 to 400 μm.

In a preferred embodiment of the invention, the resins used in steps (1), (2) and (3) are gel-type resins.

Manufacturers of the resins are for example Finex, Dow, Bayer, Purolite and Rohm & Haas.

In one embodiment of the invention, each resin is present in a separate column. In another embodiment of the invention, two or more of the different resins (SAC, WAC, SBA and WBA) may be included into one column as partial packing material beds, whereby a column includes two or more partial columns each containing a different resin.

In the chromatographic fractionation operation, the cations/anions of the resin are preferably in substantial equilibrium with the cations/anions of the feed solution of the system.

The eluent used in the chromatographic fractionation is preferably water, but even solutions of salts and water are useful. Furthermore, alcohols, such as ethanol, and mixtures of water and an alcohol, such as a mixture of water and ethanol and evaporation condensates are useful eluents.

The temperature of the chromatographic fractionation is typically in the range of 20 to 90° C., preferably 40 to 65° C. The pH of the solution to be fractionated is typically in the range of 2 to 9.

The chromatographic fractionation may be carried out as a batch process or a simulated moving bed process (SMB process). The SMB process is preferably carried out as a sequential or continuous process.

In the simulated moving bed process, the chromatographic fractionation is typically carried out using 3 to 14 columns connected in series and forming at least one loop. The columns are connected with pipelines. The flow rate in the columns is typically 0.5 to 10 $m^3/(hm^2)$ of the cross-sectional area of the column. The columns are filled with a column packing material selected from the resins described above. The columns are provided with feed lines and product lines so that the feed solution and the eluent can be fed into the columns and the product fractions collected from the columns. The product lines are provided with on-line instruments so that the quality/quantity of the production flows can be monitored during operation.

During the chromatographic SMB separation, the feed solution is circulated through the columns in the loops by means of pumps. Eluent is added, and the product fraction containing the desired deoxy sugar, other optional product fractions and residual fractions are collected from the columns. The flow of the eluent in the columns may be effected from the top of the columns or from the bottom of the columns.

Before the chromatographic fractionation, the feed solution may be subjected to one or more pretreatment steps selected from softening by ion-exchange treatment or dilution, concentration e.g. by evaporation, pH adjustment and filtration, for example. Before feeding into the columns, the feed solution and the eluent are heated to the fractionation temperature described above (for instance in the range of 50 to 85° C.).

The chromatographic fractionation provides one or more fractions enriched in at least one deoxy sugar.

To improve the yield of the chromatographic fractionation, recycle fractions of the chromatographic fractionation can also be used.

The chromatographic fractionation method of the invention may further comprise one or more purification steps selected from membrane filtration, ion exchange, evaporation and filtration. These purification steps may be carried out before, after or between said chromatographic fractionation steps.

The fraction enriched in the desired deoxy sugar obtained from the chromatographic fractionation may be further purified by crystallization to obtain a crystalline deoxy sugar product.

The crystallization is typically carried out using evaporation and cooling crystallization. The crystallization solvent may be selected from water, an organic solvent, such as an alcohol, preferably ethanol, and a mixture thereof.

In the following, the crystallization of deoxy sugars is described in more detail referring to the crystallization of fucose.

The crystallization of fucose is typically carried out using a solvent selected from water, an organic solvent, such as an alcohol, preferably ethanol, and mixtures thereof, such as a mixture of water and ethanol. In a preferred embodiment of the invention, the crystallization is carried out with water or with a mixture of water and ethanol.

The crystallization is typically carried out by evaporating the solution enriched in fucose, which has been obtained from the chromatographic fractionation to an appropriate dry substance content (e.g. to an RDS of about 70 to 90% depending on the solubility and composition of the liquid). The solution may be seeded with seed crystals of fucose. The seeds, if used, are pulverized crystals in a dry form or they are suspended in a crystallization solvent, which may be water, an alcohol, such as ethanol, or a mixture thereof. A typical crystallization solvent is water. The evaporation can be continued after seeding, if the crystal growth potential and viscosity allow. After evaporation, the crystallization mass may be subjected to cooling with simultaneous mixing, until the crystal content or the viscosity of the crystallization mass is sufficiently high. Then the crystallization solvent may be added if further cooling is needed to increase the yield or if lower viscosity is needed for the separation of the crystals. The crystallization mass is typically cooled to a temperature of 10 to 40° C. The crystallization mass may then be mixed at the final temperature for a period of time, preferably from 0.5 hours to 6 days to reach the maximum crystallization yield, whereafter the crystals are separated for example by filtering. The filtration can be carried out with traditional centrifuges or filters. The filtration cake is washed with the crystallization solvent and dried. Drying can be carried out for example at a temperature between 30 and 90° C. by traditional methods. Crystals of fucose with a high purity are obtained. The crystallization typically provides crystalline fucose having a purity of over 99% on DS and a melting point of over 142.5° C.

In the fractional crystallization of fucose, the crystallization provides crystalline fucose having a purity of over 60%, preferably over 90% and most preferably over 99%.

In one embodiment of the invention, the crystallization of fucose is carried out from a solution containing more than 45% fucose on DS. In another embodiment of the invention, the crystallization of fucose is carried out from a solution containing more than 80% fucose on DS. In a preferred embodiment of the invention, the crystallization of fucose is carried out from a solution further containing the following impurity profile: less than 20% rhamnose, less than 15% xylose, less than 3% arabinose and less than 1% galactose on DS.

In one embodiment of the invention, the crystallization of fucose is carried out from a solution containing more than 45% fucose in the presence of the following impurity profile: less than 20% rhamnose, less than 15% xylose, less than 3% arabinose and less than 1% galactose on DS. The crystallization is typically carried out from a mixture of water and ethanol, the viscosity of the mass is typically in the range of 5 to 500 Pas and the residence time is in the range of 0.5 to 10 days and temperature is in the range of 0 to 100° C.

In another embodiment of the invention, the crystallization of fucose is carried out from a solution containing more than 80% fucose in the presence of the impurity profile presented above. The crystallization is carried out for a period of 6 to 80 hours in the temperature range of 0 to 100° C. and it can be carried out without organic solvents.

In a further aspect of the invention, the invention also provides a process for the crystallization of fucose, where the crystallization of fucose is carried out from a biomass-derived solution containing more than 45% fucose in the presence of an impurity profile comprising less than 20% rhamnose, less than 15% xylose, less than 3% arabinose and less than 1% galactose on DS.

In a still further aspect of the invention, the invention also provides a process for the crystallization of fucose, where the crystallization of fucose is carried out from a biomass-derived solution containing more than 80% fucose in the presence of an impurity profile comprising less than 20% rhamnose, less than 15% xylose, less than 3% arabinose and less than 1% galactose on DS.

The desired impurity profile of the crystallization feed described above may be achieved for example by chromatographic fractionation, fractional crystallization of a biomass hydrolyzate or by mixing liquids having different compositions, which are preferably prepared by steps (1) to (3) described above.

The process of the invention typically comprises a further step of washing the crystals obtained from the crystallization. The washing agent is typically selected from water and organic solvents, such as ethanol, or mixtures thereof.

A typical dry substance content of the crystallization feed is in the range of 30 to 70% by weight. A suitable viscosity of the fucose crystallization mass is 50 to 300 Pas.

In a still further aspect of the invention, the invention also provides a novel crystalline fucose product having a melting point higher than 141° C. and most preferably higher than 142.5° C. and purity higher than 99% on DS. Said novel crystalline fucose product may be obtained by methods presented above, especially by crystallizing fucose from a solution containing more than 45% fucose, typically more than 80% fucose, and in the presence of the impurity profile presented above.

The starting material for the recovery of deoxy sugars is typically a mixture containing said deoxy sugars, other monosaccharides and other carbohydrates. In a typical embodiment of the invention, said deoxy sugars comprise methyl-α-D-xylose, rhamnose and fucose. The mixture may also contain disaccharides and higher saccharides.

The starting material for the recovery of deoxy sugars is derived from biomass, typically from a hemicellulose-containing plant-based material, such as softwood or hardwood, grain straw or hulls, corn husks, corn cops, corn fibers, bagasse and sugar beet. Hemicellulose-containing biomass derived from hardwood, such as birch or beech, is especially preferred for use as the starting material in the present invention.

The starting material for the recovery of deoxy sugars is typically a hydrolyzate of the above-described hemicellulose-containing biomass. The hydrolyzate has been typically obtained from mild acid hydrolysis or enzymatic hydrolysis of the biomass. In a preferred embodiment of the invention, the starting material is a hemicellulose hydrolyzate or a solution derived from a hemicellulose hydrolyzate.

The biomass hydrolyzate for the recovery of deoxy sugars in accordance with the present invention is typically spent liquor obtained from a pulping process. The spent liquor is especially spent sulfite pulping liquor, which may be obtained by acid, basic or neutral sulfite pulping, preferably acid sulfite pulping.

A typical spent liquor useful in the present invention is spent liquor, which is preferably obtained from acid sulfite pulping. The spent liquor may be obtained directly from sulfite pulping. It may also be concentrated sulfite pulping liquor or a side-relief obtained from sulphite cooking. It may also be a fraction which has been chromatographically obtained from sulfite pulping liquor and which contains deoxy sugars.

The starting solution containing deoxy sugars may be e.g. spent sulfite pulping liquor, from which the main part of xylose, rhamnose and/or mannose have been separated, for example a liquor disclosed in WO 02/27039 (US publication No. 02/0120135).

In one typical embodiment of the invention, the starting solution contains, in addition to deoxy sugars, ordinary sugars, such as aldose sugars typically derived from the hemicelluloses of the biomass.

In another typical embodiment of the invention, the starting solution is a side stream which has been separated from a xylose recovery process after the recovery of xylose or a rhamnose recovery process after the recovery of rhamnose and which is enriched in deoxy sugars. Such a side stream may be for example mother liquor from a crystallization process step or a by-product fraction from a chromatographic separation process step or the like. The rhamnose recovery process mentioned above refers to a process of recovering rhamnose for example from sulfite spent liquor after the recovery of xylose (WO 02/270039). By using a weakly acid cation exchange resin as the column filling material, deoxy sugars such as rhamnose can be separated from hexose and pentose sugars. By using a weakly acid cation exchange resin in $Na^+$ form at an elevated pH, rhamnose is eluted before hexose and pentose sugars.

The starting material may also be a solution derived from sugar beet or sugar cane.

The following examples represent illustrative embodiments of the invention without limiting the invention in any way.

In the following examples, rhamnose and fucose are in L-form.

EXAMPLE 1

Chromatographic Fractionation of a Solution Containing Deoxy Sugars with a Strongly Acid Cation Exchange Resin in $Na^+$ form The solution containing deoxy sugars used as the feed for the chromatographic separation was a side stream separated from $Ca^{2+}$ based sulfite spent liquor after the recovery of the main part of xylose (WO 02/27039; US publication No. 02/0120135). Birch had been used as raw material for the sulfite cooking. The feed solution had the following composition:

| Composition of the feed | |
|---|---|
| Dry solids, g/100 ml | 42 |
| Fucose, % on RDS | 5.7 |
| Rhamnose, % on RDS | 23.2 |
| MAX, % on RDS | 13.0 |
| Others, % on RDS | 58.1 |

The chromatographic fractionation was performed in a pilot scale chromatographic separation column as a batch process. The column with a diameter of 1 m was filled with a strongly acid cation exchange resin having a styrene skeleton (Finex CS 0.11GC), manufactured by Finex Ltd. The resin was in $Na^+$ form. The height of the resin bed was approximately 4.8 m. The DVB-content of the resin was 5.5 weight-% and the average particle size of the resin was 0.307 mm. The temperature of the column, the feed solution and the eluent water was 65° C. The flow rate in the column was adjusted to 550 l/h.

The chromatographic fractionation was carried out as follows:

Step 1: The dry substance of the feed solution was adjusted to 37 g dry substance in 100 g solution according to the refractive index (RI) of the solution.

Step 2: 60 l of preheated feed solution was pumped to the top of the resin bed.

Step 3: The feed solution was eluted downwards in the column by feeding preheated ion-exchanged water to the top of the column.

Step 4: 50-ml samples of the out-coming solution were collected at 5 min intervals. The composition of the samples was analyzed with HPLC equipment with Refractive Index detector and two times amino column (75% ACN was used as the eluent).

Rhamnose was eluted from the column before fucose and MAX, and fucose and MAX were eluted almost at the same time. A fraction rich in rhamnose and a fraction rich in fucose and MAX may be separated with the purities and yields presented in the table below. The yield of a component in a fraction is presented in relation to the total amount of that component in all out-coming fractions, including also the recycle fractions and residual fractions.

| | Rhamnose fraction | Fucose and MAX fraction |
|---|---|---|
| Compositions | | |
| Rhamnose % on RDS | 44.9 | 15.4 |
| Fucose % on RDS | 0.6 | 10.4 |
| MAX % on RDS | 1.3 | 24.5 |
| Yields | | |
| Rhamnose % | 50 | 27.7 |
| Fucose % | 3 | 78.1 |
| MAX % | 2.7 | 84.4 |

The fraction rich in rhamnose may be added to further processing of rhamnose.

The pH of the effluent (the out-coming solution) was 4–6. The separation profile is presented in FIG. 1.

EXAMPLE 2

Chromatographic Fractionation of a Solution Containing Deoxy Sugars with a Strongly Acid Cation Exchange Resin in $Zn^{2+}$ form The feed solution used for the chromatographic fractionation had been obtained from the rhamnose recovery process disclosed in WO 02/0120135 (US Publication No. 02/0120135). The feed solution had the following composition:

| Composition of the feed | |
|---|---|
| Dry solids, g/100 g | 25 |
| Fucose, % on RDS | 13.0 |
| Rhamnose, % on RDS | 9.2 |
| MAX, % on RDS | 37.0 |
| Others, % on RDS | 70.8 |

The chromatographic fractionation was performed in a laboratory chromatographic separation column as a batch process. The column with a diameter of 0.09 m was filled with a strongly acid cation exchange resin having a styrene skeleton (Finex CS 11 GC), manufactured by Finex Ltd. The height of the resin bed was approximately 1.5 m. The DVB-content of the resin was 5.5 weight-% and the average particle size of the resin was 0.307 mm. The resin was regenerated into $Zn^{2+}$-form. The temperature of the column and feed solution and eluent water was 65° C. The flow rate in the column was adjusted to 50 ml/min.

The chromatographic fractionation was carried out as follows:

Step 1: The dry substance of the feed solution was adjusted to 25 g dry substance in 100 g solution according to the refractive index (RI) of the solution.

Step 2: 800 ml of preheated feed solution was pumped to the top of the resin bed.

Step 3: The feed solution was eluted downwards in the column by feeding preheated ion-exchanged water to the top of the column.

Step 4: 10-ml samples of the out-coming solution were collected at 3 min intervals. The composition of the samples was analyzed with Dionex HPLC equipment with a pulsed electrochemical detector and CarboPac PA1™ anion exchange column (water and 0.2 M NaOH were used as eluents).

Rhamnose was eluted before fucose and MAX, and fucose and MAX were eluted almost at the same time. A fraction rich in rhamnose and a fraction rich in fucose and MAX may be separated with the purities and yields presented in the table below.

| | Rhamnose fraction | Fucose and MAX fraction |
|---|---|---|
| Compositions | | |
| Rhamnose % on RDS | 20.2 | 4.1 |
| Fucose % on RDS | 7.7 | 15.4 |
| MAX % on RDS | 7.3 | 45.4 |
| Yields | | |
| Rhamnose % | 56.6 | 43.4 |
| Fucose % | 11.7 | 88.3 |
| MAX % | 4.1 | 95.9 |

Figure 2:
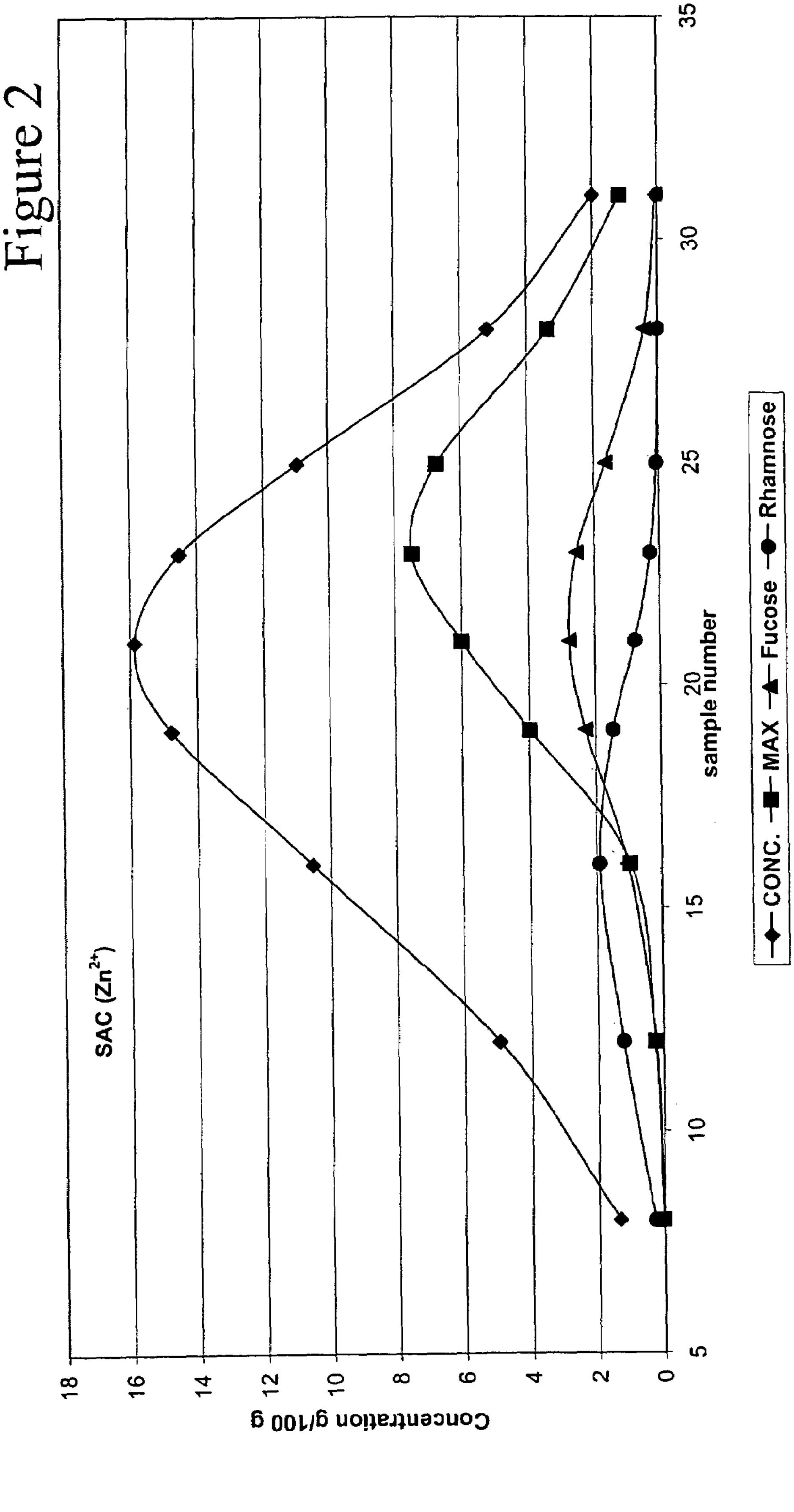
FIG. 2 is a graphical presentation of the separation profile obtained from Example 2 (chromatographic fractionation of a solution containing deoxy sugars with a strongly acid cation exchange resin in $Zn^{2+}$ form).

The pH of the effluent (e.g. the out-coming solution) was between 3 and 4. The separation profile is presented in FIG. 2.

EXAMPLE 3

Chromatographic Fractionation of a Solution Containing Deoxy Sugars with a Weakly Acid Cation Exchange Resin in $Na^+$ form The feed solution used for the chromatographic fractionation was a fraction containing fucose, MAX, rhamnose and other monosaccharides obtained in accordance with Example 1 (separation with SAC in $Na^+$ form). The feed solution had the following composition:

| Composition of the feed | |
|---|---|
| Dry solids, g/100 ml | 36.7 |
| Fucose, % on RDS | 12.6 |
| Rhamnose, % on RDS | 14.8 |
| MAX, % on RDS | 21.2 |
| Others, % on RDS | 51.4 |

The chromatographic fractionation was performed in a pilot scale chromatographic separation column as a batch process. The column with a diameter of 0.60 m was filled with a weakly acid cation exchange resin having an acrylic skeleton (Finex CS 16GC), manufactured by Finex Ltd. The resin was regenerated to $Na^+$-form. The height of the resin bed was approximately 5.2 m. The DVB-content of the resin was 8 weight-% and the average particle size of the resin was 0.33 mm. The temperature of the column, the feed solution and the eluent water was 65° C. The flow rate in the column was adjusted to 150 l/h.

The chromatographic fractionation was carried out as follows:

Step 1: The dry substance of the feed solution was adjusted to 33 g dry substance in 100 g solution according to the refractive index (RI) of the solution.

Step 2: 150 l of preheated feed solution was pumped to the top of the resin bed.

Step 3: The feed solution was eluted downwards in the column by feeding preheated ion-exchanged water to the top of the column.

Step 4: Fraction samples of the out-coming solution were collected at 8-min intervals. The composition of the samples was analyzed with HPLC equipment with a Refractive Index detector and two times an amino column (75% ACN was used as the eluent).

The elution order was methyl-α-D-xylose (MAX), rhamnose and fucose, and they were partially overlapping. Some of the other monosaccharides are eluted as a separate peak after fucose. With a $Na^+$ form WAC resin fraction rich in each of the above mentioned components could be separated as presented in the table below.

| | Rhamnose fraction | Fucose fraction | MAX fraction |
|---|---|---|---|
| Compositions | | | |
| Rhamnose % on RDS | 26.8 | 9 | 11.6 |
| Fucose % on RDS | 17.6 | 32 | 2.1 |
| MAX % on RDS | 4.1 | 1.3 | 47.5 |
| Yields | | | |
| Rhamnose % | 48.6 | 13.4 | 35.7 |
| Fucose % | 35.4 | 53.1 | 7.3 |
| MAX % | 4.6 | 1.2 | 91.7 |

Figure 3:
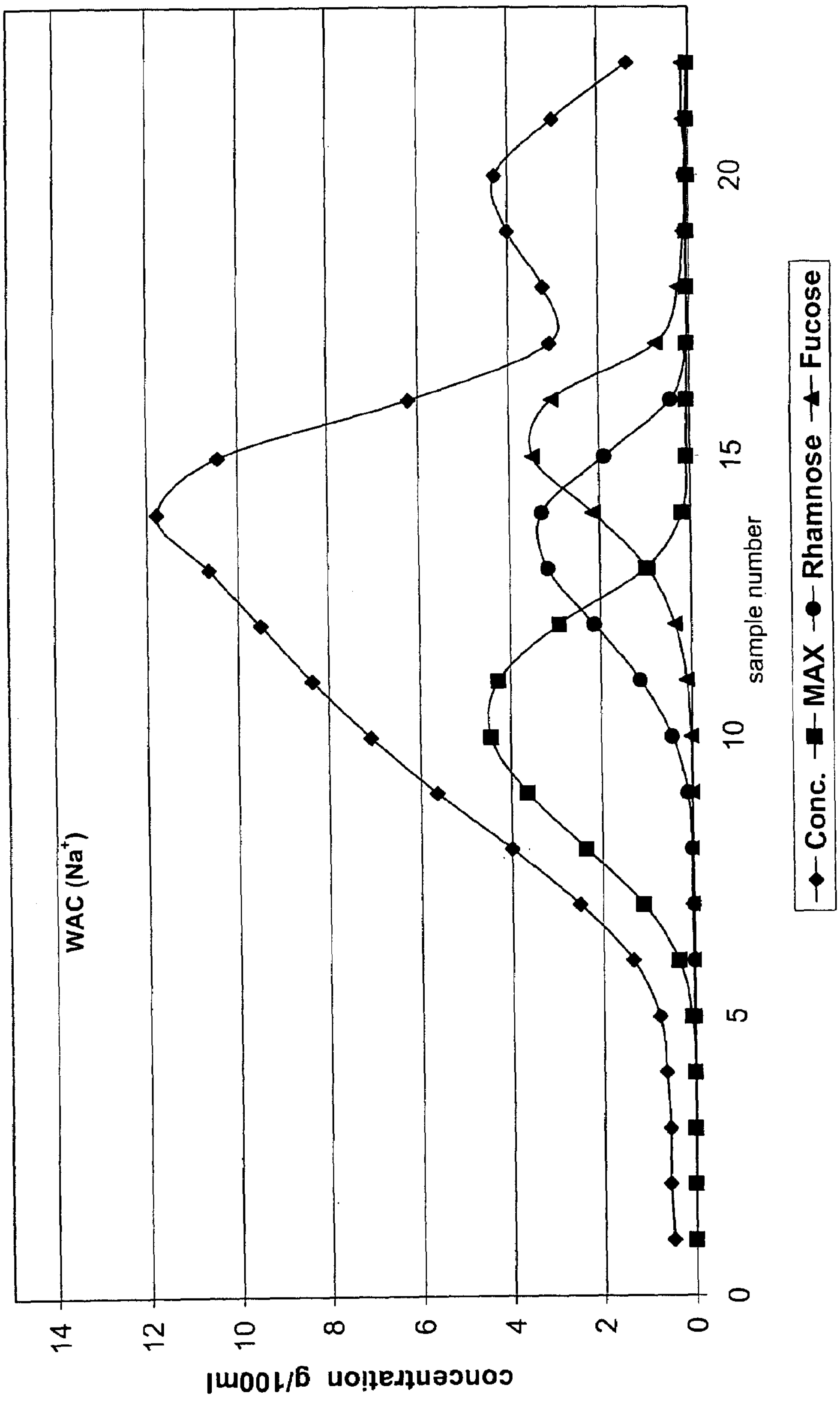
FIG. 3 is a graphical presentation of the separation profile obtained from Example 3 (chromatographic fractionation of a solution containing deoxy sugars with a weakly acid cation exchange resin in $Na^+$ form).

The pH of the effluent was between 9.2 and 9.7. The separation profile is presented in FIG. 3.

EXAMPLE 4

Pretreatment of a Solution Containing Deoxy Sugars with a Strongly Basic Anion Exchange Resin in $HSO_3^-$ form The pretreatment step was performed in a pilot scale chromatographic separation column as a batch process. The column with a diameter of 0.225 m was filled with a strongly basic anion exchange resin having an acrylic skeleton (Duolite A 101 D). The mean bead size was 0.35 mm. The height of the resin bed was approximately 3.5 m. The resin was regenerated into bisulfite ($HSO_3^-$) form and a feeding device was placed at the top of the resin bed. The temperature of the column and feed solution was 25° C. The flow rate in the column was adjusted to be at maximum 20 l/hour. The pH of the feed solution was in the range of 4 to 4.5.

As the feed, syrup from Example 3 (WAC ($Na^+$)) was used, and the aim of this pretreatment was to remove those compounds that could displace $HSO_3^-$ ions from the chromatographic separation resin.

The pretreatment step was carried out as follows:

Step 1: Eluent water level was dropped down until a short layer of water could be seen on top of the resin surface.

Step 2: 1500–2000 liters of feed solution was run through the column.

Step 3: Feed solution level was dropped down until a short layer of solution could be seen on top of the resin surface.

Step 4: Eluent water was run through the column until no dry substance could be measured in the output.

The pretreatment step did not increase the deoxy sugar purity, neither can there be seen any decomposing. Color removal from the fucose fraction and the stability effect in the following separations was significant. The pH of the out-coming solution was about 4.

EXAMPLE 5

Chromatographic Fractionation of a Solution Containing Deoxy Sugars with a Strongly Basic Anion Exchange Resin in $HSO_3^-$ form The feed solution used for the chromatographic fractionation was a fraction containing deoxy sugars obtained in accordance with Example 3 (separation with WAC in $Na^+$ form). The feed solution had the following composition:

| Composition of the feed | |
|---|---|
| Dry solids, g/100 ml | 42.5 |
| Fucose, % on DS | 47.9 |
| Rhamnose, % on DS | 10.5 |
| MAX, % on DS | 2.2 |
| Others, % on DS | 39.4 |

The chromatographic fractionation was performed in a pilot scale chromatographic separation column as a batch process. The column with a diameter of 0.6 m was filled with a strongly basic anion exchange resin having an acrylic skeleton (Finex As 532 GC, 3.5% DVB). The height of the resin bed was approximately 4.8 m. The average particle size of the resin was 0.35 mm. The resin was regenerated into bisulfite ($HSO_3^-$) form. The temperature of the column, the feed solution and the eluent water was 40° C. The flow rate in the column was adjusted to 283 l/h.

The chromatographic fractionation was carried out as follows:

Step 1: The dry substance of the feed solution was adjusted to 37 g dry substance in 100 g solution according to the refractive index (RI) of the solution.

Step 2: 100 l of preheated feed solution was pumped to the top of the resin bed.

Step 3: The feed solution was eluted downwards in the column by feeding preheated ion-exchanged water to the top of the column.

Step 4: 50-ml samples of the out-coming solution were collected at 10 min intervals. The composition of the samples was analyzed with HPLC equipment having an amino column; ACN (79%) was used as the eluent.

Most of the other monosaccharides including MAX were eluted from the column as a separate peak before fucose and rhamnose. Rhamnose was eluting from the column after fucose, but they were partially overlapping. With a bisulfite-form strongly basic anion exchange resin, fractions rich in fucose and rhamnose may be separated as presented in the table below.

| | Fucose fraction | Rhamnose |
|---|---|---|
| Compositions | | |
| Rhamnose % on RDS | 6.4 | 70.2 |
| Fucose % on RDS | 82.6 | 20.8 |
| Yields | | |
| Rhamnose % | 39.6 | 60.4 |
| Fucose % | 94.7 | 3.3 |

Figure 4:
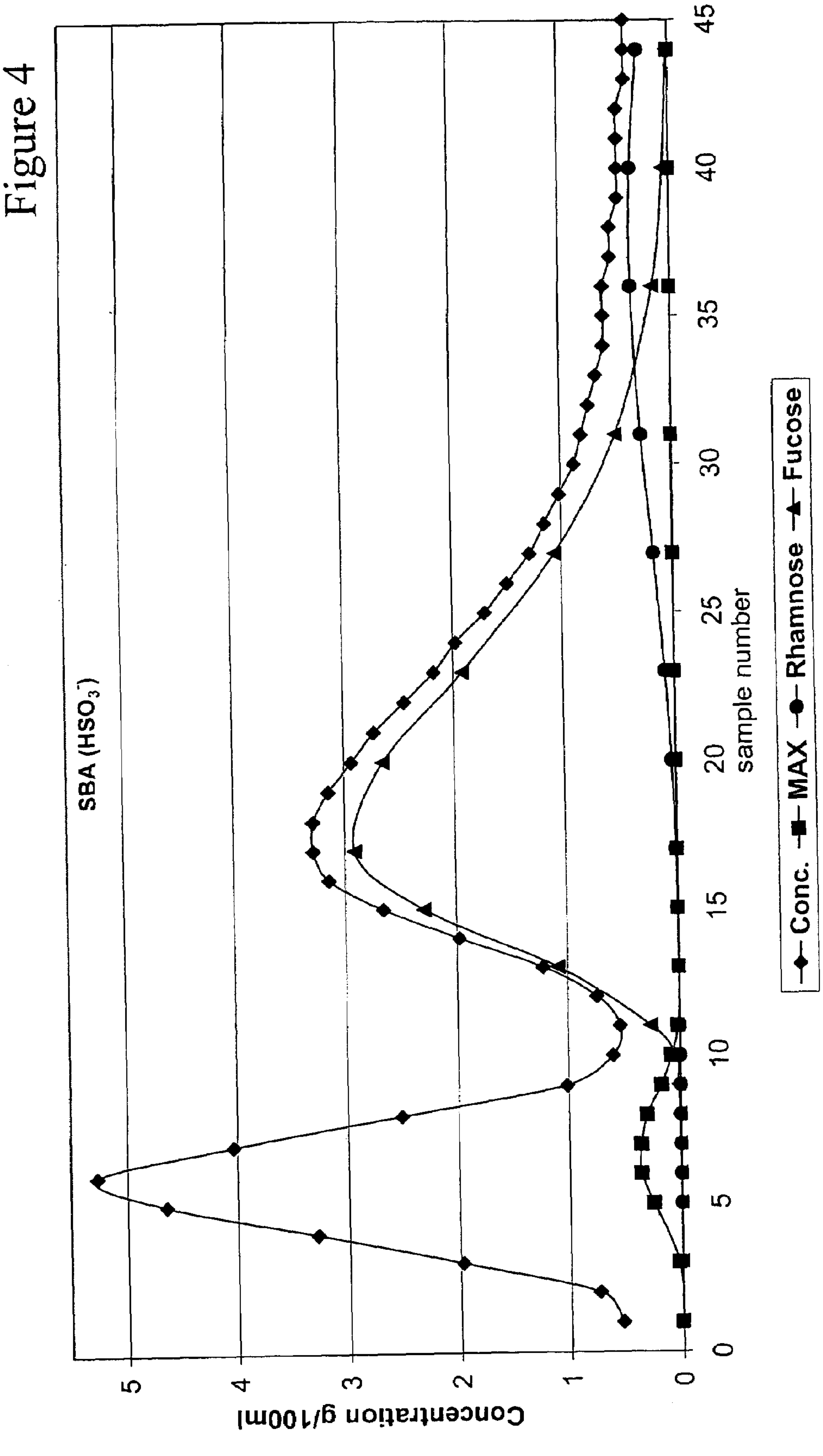
FIG. 4 is a graphical presentation of the separation profile obtained from Example 5 (chromatographic fractionation of a solution containing deoxy sugars with a strongly basic anion exchange resin in $HSO_3^-$ form).

The pH of the effluent (e.g. the out-coming solution) was 4.0–4.3. The separation profile is presented in FIG. 4.

EXAMPLE 6

Cooling Crystallization of Fucose (Aqueous Crystallization Continued by Crystallization in a Mixture of EtOH and Water)

Cooling crystallization was carried out from chromatographically enriched fucose syrup containing 71.8% fucose, 1.4% xylose, 0.9% arabinose, 5.3% rhamnose and less than 0.2% galactose on DS. A total of 55 kg dry substance of the feed syrup was concentrated by evaporation at reduced pressure and transferred into a 100-liter cooling crystallizer. The syrup having a dry substance content of 89.3% by weight was mixed at 50° C. The seeding occurred spontaneously during mixing. After about 20 hours' mixing at 50° C., the mother liquor had a dry substance concentration of 85.3% by weight corresponding to a fucose crystallization yield of 29%. Then 25 liters ethanol was added to reduce the viscosity and the mass was cooled to 20° C. in 40 hours. The crystallization mass was mixed for 3 days at about 20° C. to obtain maximum fucose crystallization yield. The crystals were then separated from the mother liquor using a traditional basket centrifuge. A total of 26.5 kg wet crystals was obtained. The crystals were washed by mixing with 20 liters ethanol, centrifuged and dried. A total of 24.5 kg fucose crystals with a purity of more than 99% was obtained. The yield of the fucose was 62% of the fucose in the feed syrup. The fucose product had a melting point of 145.1° C.

Three melting point measurements were made by the European Pharmacopoeia method both before and after grinding. The melting point results from the dried crystals were 145.0, 145.0 and 144.6° C. and from the finely powdered sample 145.2, 145.4 and 145.4° C. The average of all the measurements was 145.1° C. In addition, thermal behavior was measured by a Differential Scanning Calorimeter (Mettler FP84HT) by using a 2° C./min heating rate from 40° C. to 160° C. There was one peak in the thermogram and the peak temperature was 143.5° C.

EXAMPLE 7

Crystallization of Fucose with Water as Solvent (Aqueous Boiling Crystallization Followed by Cooling Crystallization in Water)

The starting material for the crystallization was a fraction enriched in fucose, obtained in accordance with Example 5, i.e. from three sequential chromatographic fractionations (SAC in $Na^+$ form, WAC in $Na^+$ form and SBA in $HSO_3^-$ form). The starting fucose solution contained 86.3% fucose, 0.8% xylose, 0.3% arabinose, 4.5% rhamnose and less than 0.2% galactose on DS. Some low purity intermediate fucose crystals from a previous crystallization were dissolved and mixed with the starting solution to obtain the crystallization feed liquid. The composition of the feed liquid thus obtained was 88.3% fucose, 1.1% xylose, 0.3% arabinose and 4.1% rhamnose, 0.2% galactose and less than 0.5% MAX on DS, measured by HPLC (the resins in an amino form, +55° C., 79% ACN with 50% $H_3PO_4$ 6 ml/l). The pH of the feed solution was 4.3 and the dry substance content (DS) was 34.1% w/w. Totally 280 kg DS of the feed syrup was concentrated by a traditional evaporative crystallizer at reduced pressure. The seeding was carried out with 40 grams of dry pulverized fucose seed crystals at 54.5° C. The seed crystals were prepared by grinding from the product of the previous crystallization. After seeding, the boiling crystallization mass was prepared by feeding the rest of the syrup and by concentrating the crystallization mass at a reduced pressure. Totally 240 liters of the boiling crystallization mass was transferred into a traditional cooling crystallizer. The mass was cooled gradually from 55 to 23.5° C. in 40 hours. After about 9 hours' mixing at 23.5° C. the crystallization yield was approximately 59% of fucose. The course of the crystallization was the following:

| Time hrs | T ° C. | DS, ml % w/w | |
|---|---|---|---|
| 0 | 54.5 | 80.4 | Seeding with 40 g seed crystals into the evaporative crystallizer |
| 2 | 55.0 | 82.1 | Starting the cooling crystallization (DS, mass 83.0) |
| 22 | 40.7 | 75.3 | |
| 42 | 23.0 | 70.8 | Cooling finished |
| 51 | 23.5 | 70.7 | Centrifuging, crystal washing and drying test |

One centrifuging test was made with a laboratory basket centrifuge Roto Silenta II (7 min/3350 rpm, 50 ml washing water). Totally 483 grams of wet crystals were obtained from 1155 grams of the crystallization mass. The centrifuging results were the following:

| | Total g | DS % | Fucose % on DS | DS g |
|---|---|---|---|---|
| Crystallization mass | 1155 | 83.0 | 86.3 | 958.7 |

-continued

| | Total g | DS % | Fucose % on DS | DS g |
|---|---|---|---|---|
| Centrifuged crystals | 483 | 97.6 | 98 | 471.4 |

The drying (about 6 h at 40° C.) resulted in 2.4% loss of drying. The crystal purity was 98% on DS and the melting point was 136.6° C. The fucose yield was 54.6% based on the amount of the available fucose. Some of the centrifuged crystals were washed by mixing with 99.5% ethanol, centrifuged and dried. As a result, a crystalline product with a purity of more than 99% and a melting point of 146.1° C. was obtained. The product yield of the fucose crystals having a purity of more than 99% was about 50%. This example demonstrates that high purity fucose crystals can be obtained by crystallization from a water solution when the composition of the feed liquid is within the critical limits and when the impurities are not precipitated, but can be washed off from the crystals with the mother liquor.

EXAMPLE 8

Crystallization of Fucose with a Mixture of Water and Ethanol as Solvent (Aqueous Boiling Crystallization Followed by Cooling Crystallization in a Mixture of EtOH and Water)

The feed syrup for the crystallization was the same fucose solution as in Example 7. The beginning of the crystallization was carried out in the same way as in Example 7. The boiling crystallization described in Example 6 was continued by cooling crystallization in a water solvent, until the crystal content made the viscosity high. Then 30 liters of 99.5% ethanol was mixed into the crystallization mass to reduce the viscosity and the crystallization was continued by cooling from 23.5 to 15.5° C. in 15 hours. Then the crystals were separated from the mother liquor by using a traditional basket centrifuge. Totally 154.5 kg wet crystals were obtained. The crystals were washed by mixing with 100 liters of 99.5% ethanol, centrifuged and dried. Totally 121.5 kg of a crystalline product with a purity of more than 99% and a melting point of 145.5° C. was obtained. The specific optical rotation was $[\alpha]_D^{20}$−74.7°. The yield of the fucose product was about 50%. This example demonstrates that high purity fucose crystals can be obtained by crystallization from a mixture of EtOH and water, when the composition of the feed liquid is within the critical limits.

EXAMPLE 9

Crystallization of Fucose with a Mixture of Water and Ethanol as Solvent (Aqueous Boiling Crystallization Followed by Cooling Crystallization in a Mixture of EtOH and Water)

The starting material for the crystallization was obtained by combining the mother liquors and washings from the crystallizations of Examples 7 and 8. The feed solution contained about 78% fucose, 1.8% xylose, 0.6% arabinose, 7.8% rhamnose, 0.5% galactose and less than 0.5% MAX on DS (measured by HPLC: resins in an amino form, +55° C., 79% ACN with 50% $H_3PO_4$ 6 ml/l). Totally 138 kg DS of the feed syrup with a DS content of 43% by weight (w/w) was concentrated by a traditional evaporative crystallizer at a reduced pressure. The seeding was carried out with 40 grams of the fucose seed crystals at 54.6° C. After seeding, the boiling crystallization mass was prepared by feeding the rest of the syrup and by concentrating the crystallization mass at a reduced pressure. Totally 115 liters of the boiling crystallization mass was transferred into a traditional cooling crystallizer. The mass was cooled gradually from 56 to 36° C. in 48 hours, whereby the viscosity became high and the mass was suitable for crystal separation from a water solvent. At this stage, the crystallization yield was 50% fucose. However, the crystallization was continued by adding 27 liters 99.5% ethanol to reduce the viscosity and by cooling from 36 to 15.5° C. in 20 hours. Then the crystals were separated and dried. The course of the crystallization was the following:

| Time hrs | T ° C. | DS, ml % w/w | |
|---|---|---|---|
| 0 | 54.6 | 83.3 | Seeding with 40 g seed crystals in an evaporative crystallizer |
| 1 | 56.0 | 82.1 | Cooling crystallization started. DS, mass 85.0 |
| 20 | 51.3 | 79.6 | |
| 48 | 36.0 | 77.8 | The mass was thick and EtOH addition was started |
| 67 | 15.5 | — | Centrifuging, crystal washing and drying |

The crystals were separated from the mother liquor by using a traditional basket centrifuge. Totally 59.9 kg wet crystals were obtained. The crystals were washed by mixing with 30 liters of 99.5% ethanol, centrifuged and dried. Totally 48.4 kg of a crystalline product with a purity of more than 99% and a melting point of 143.7° C. was obtained. The specific optical rotation was $[\alpha]_D^{20}$−72.2°. The yield of the fucose product was about 48%. This example demonstrates that high purity fucose could be obtained by crystallization from a mixture of water and ethanol and directly from a feed syrup having a relatively low purity (mother liquor of the first crystallization), when the composition of the feed liquid is within critical limits.

EXAMPLE 10

Conclusion of the Fucose Crystallization Test Results

Figure 5:
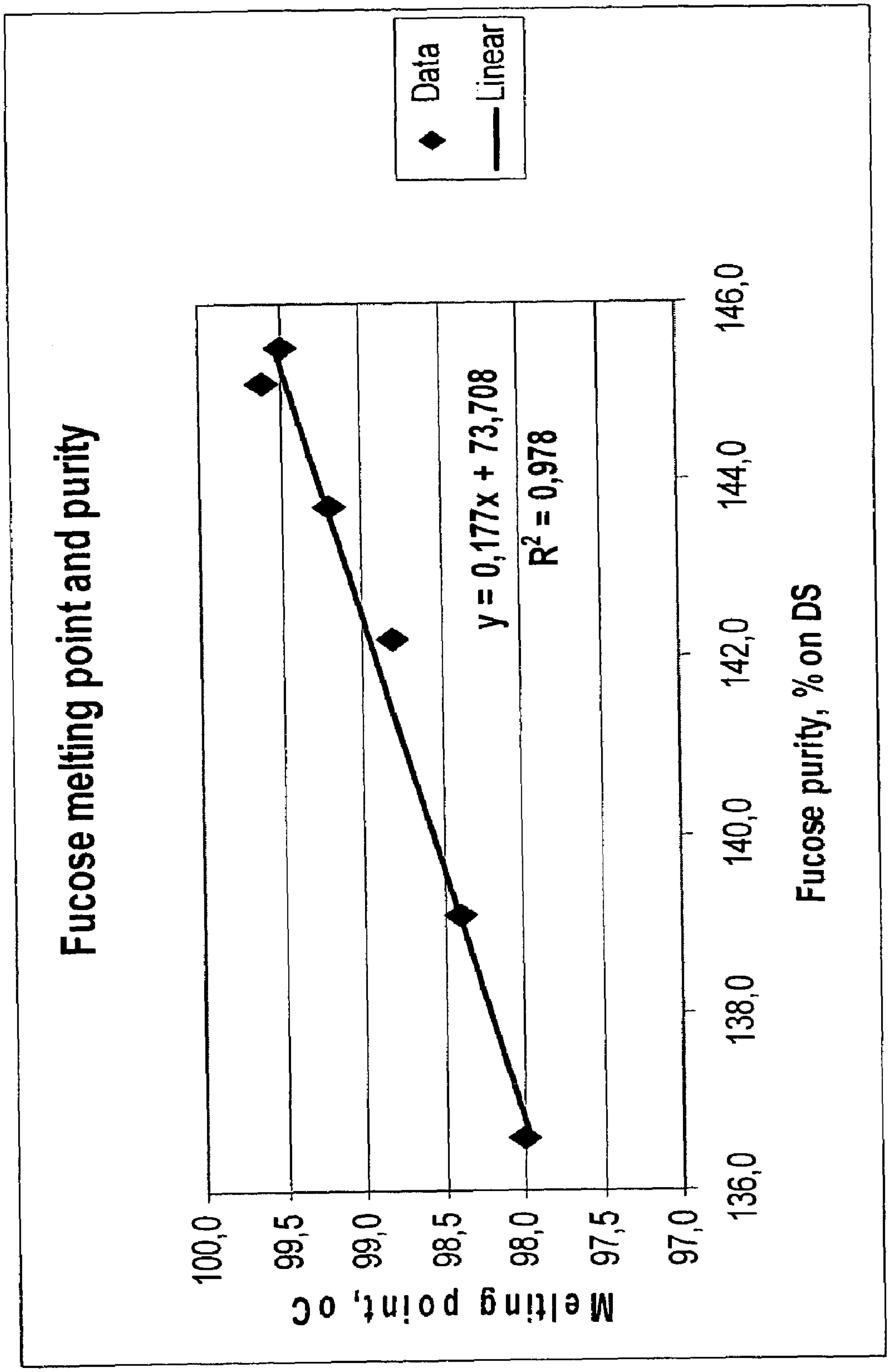
FIG. 5 is a graphical presentation showing the relation between the melting point of fucose and the purity of fucose.

It was found that the melting point is a good indication of the purity of the fucose crystals. The results are in the following table. The linear fit (see FIG. 5) of the results gives the following equation: crystal purity (% on DS)=0,177×mp (° C.)+73,71 ($R^2$=0.978).

| | m.p (° C.) | Purity (% on DS) |
|---|---|---|
| Ex 6, no extra wash | 136.6 | 98.0 |
| Example 7 | 145.5 | 99.5 |
| Example 8 | 143.7 | 99.2 |
| Example 9 | 145.1 | 99.6 |
| Test sample 27052 | 139.1 | 98.4 |
| Test sample 17052 | 142.2 | 98.8 |

EXAMPLE 11

Chromatographic Fractionation of a Solution Containing Deoxy Sugars with a Strongly Basic Anion Exchange Resin in $HSO_3^-$ form The solution containing deoxy sugars used as the feed for the chromatographic separation was a side stream separated from $Ca^{2+}$ based sulphite spent liquor after the recovery of the main part of xylose. Birch had been used as raw material for the sulphite cooking. The feed solution had the following composition:

| Composition of the feed | |
|---|---|
| Dry solids, g/100 ml | 35.2 |
| Fucose, % on RDS | 4.2 |
| Rhamnose, % on RDS | 17.5 |
| MAX, % on RDS | 10.3 |
| Others, % on RDS | 68 |

The chromatographic fractionation was performed in a pilot scale chromatographic separation column as a batch process. The column with a diameter of 0.1 m was filled with a strongly basic anion exchange resin having an acrylic skeleton (Finex As 532 GC, 3.5% DVB). The height of the resin bed was approximately 1.2 m. The average particle size of the resin was 0.35 mm. The resin was regenerated into bisulphite ($HSO_3^-$) form. The temperature of the column, the feed solution and the eluent water was 40° C. The flow rate in the column was adjusted to 100 ml/min. The pH of the feed solution was 6.0.

The chromatographic fractionation was carried out as follows:

Step 1: The dry substance of the feed solution was adjusted to 31.5 g dry substance in 100 g solution according to the refractive index (RI) of the solution.

Step 2: 800 ml of preheated feed solution was pumped to the top of the resin bed.

Step 3: The feed solution was eluted downwards in the column by feeding preheated ion-exchanged water to the top of the column.

Step 4: 5 ml samples of the out-coming solution were collected at 5 min intervals. The composition of the samples was analyzed with HPLC equipment having an amino column; water and ACN (79%) were used as eluents.

Figure 6:
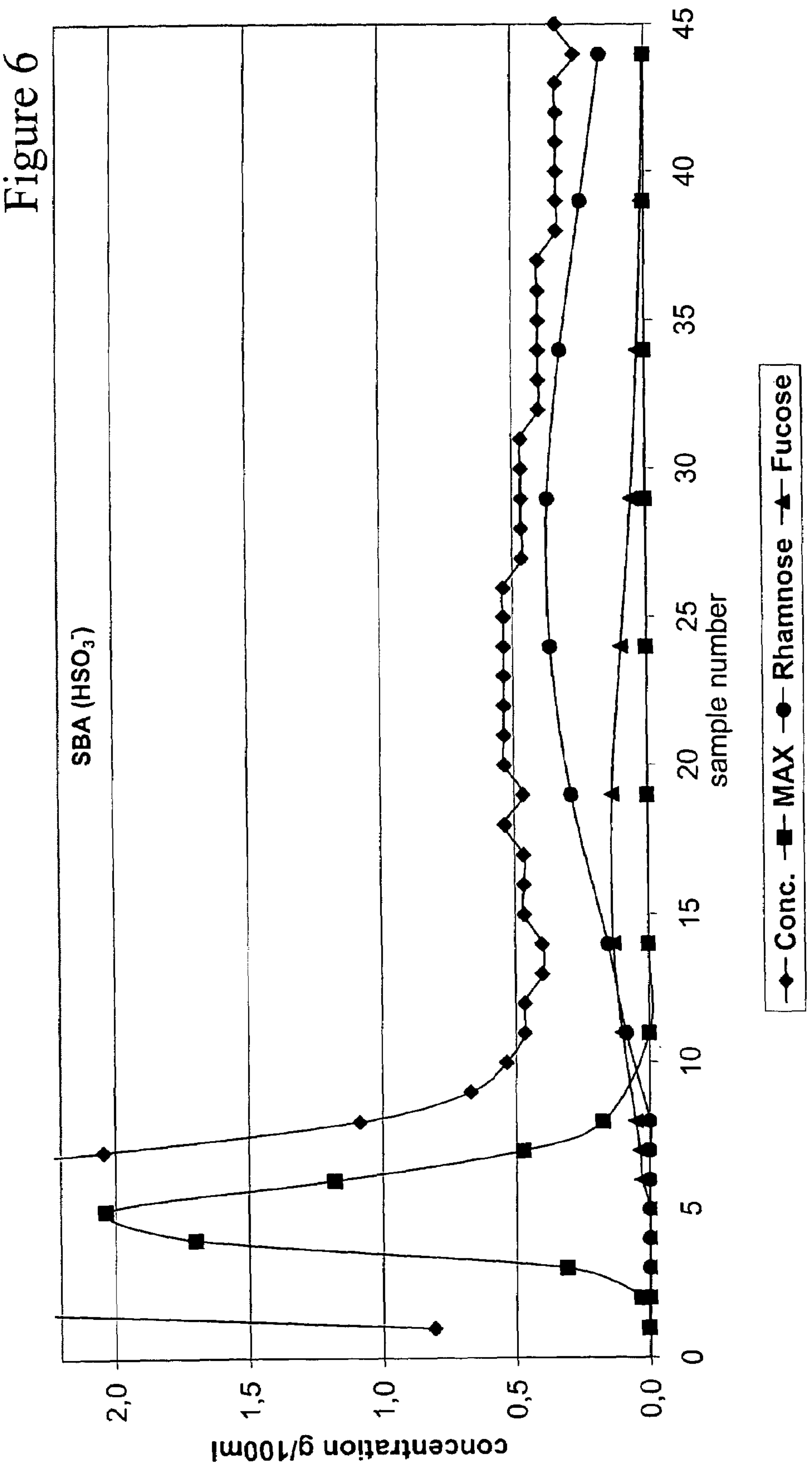
FIG. 6 is a graphical presentation of the separation profile obtained from Example 11 (chromatographic fractionation of a solution containing deoxy sugars with a strongly basic anion exchange resin in $HSO_3^-$ form.

Most of the other monosaccharides including MAX were eluting from the column as a separate peak before fucose and rhamnose. Rhamnose was eluting from the column partially after fucose. Thus with a bisulphite-form strongly basic anion exchange resin a fraction rich in fucose can be separated well from other monosaccharides and other components. The pH of the effluent (e.g. the out-coming solution) was 1.9–3.8. The separation profile is presented in FIG. 6.

EXAMPLE 12

Chromatographic Fractionation of a Syrup Containing Fucose with an SMB Process The SMB test equipment for the chromatographic fractionation included six columns connected in series, a feed pump, a recycling pump, an eluent water pump as well as inlet and product valves for the various process streams. The height of each column was 3.4 m and each column had a diameter of 0.2 m. The columns were packed with a strong acid gel type cation exchange resin (Finex CS 11 GC) in $Na^+$-form. The mean bead size was 0.33 mm and the divinylbenzene content was 5.5%.

The feed for the chromatographic fractionation was a syrup from the rhamnose recovery process disclosed in WO 02/27039 (=US 2002/120135). The aim of the chromatographic fractionation was to separate the fucose and rhamnose contained therein.

The pH of the feed was adjusted with 50% (w/w) NaOH solution to 6.2. The liquor was then filtered with a Seitz pressure filter using Kenite 300 as a filtering aid (precoat 1 $kg/m^2$, bodyfeed 0.5% on DS basis) and the feed concentration was adjusted to 55 g/100 ml. The composition of the feed is set forth in the table below, whereby the percentages are given on a dry substance weight basis.

| Composition of the feed, % on DS | |
|---|---|
| Fucose | 5.7 |
| Rhamnose | 19.1 |
| MAX | 13.8 |
| Xylose | 2.3 |
| Others | 59.1 |

The fractionation was performed by a 9-step SMB sequence as set forth below. The temperature of the feed and the eluent was 65° C. Water was used as an eluent.

Step 1: 16 l of feed solution were pumped into the first column at a flow rate of 80 l/h and a residual fraction was collected from the same column. Simultaneously 27 l of water were pumped into the second column at a flow rate of 135 l/h and a residual fraction was collected from column 4. Simultaneously also 16 l of water were pumped into column 5 at a flow rate of 80 l/h and a fucose-containing fraction was collected from the last column.

Step 2: 10 l of feed solution were pumped into the first column at a flow rate of 80 l/h and a rhamnose-containing fraction was collected from the same column. Simultaneously 19 l of water were pumped into the second column at a flow rate of 150 l/h and another rhamnose-containing fraction was collected from column 4. Simultaneously also 16 l of water were pumped into column 5 at a flow rate of 80 l/h and a fucose-containing fraction was collected from the last column.

Step 3: 30 l of feed were pumped into the first column at a flow rate of 80 l/h and a fucose-containing fraction was collected from the last column.

Step 4: 27 l of water were pumped into the last column at a flow rate of 80 l/h and a residual fraction was collected from the second column. Simultaneously 27 l of water were pumped into the third column at a flow rate of 80 l/h and a residual fraction was collected from column 5.

Step 5: 20 l of water were pumped into the last column at a flow rate of 80 l/h and a rhamnose-containing fraction was collected from the second column. Simultaneously 20 l of water were pumped into the third column at a flow rate of 80 l/h and another rhamnose-containing fraction was collected from column 5.

Step 6: 29 l were circulated in the column set loop, formed with all columns, at a flow rate of 80 l/h.

Step 7: 28 l of water were pumped into the first column at a flow rate of 80 l/h and a residual fraction was collected from the third column. Simultaneously 28 l of water were pumped into column 4 at a flow rate of 80 l/h and a residual fraction was collected from the last column.

Step 8: 20 l of water were pumped into the first column at a flow rate of 80 l/h and a rhamnose-containing fraction was collected from the third column. Simultaneously 20 l of water were pumped into column 4 at a flow rate of 80 l/h and another rhamnose-containing fraction was collected from the last column.

Step 9: 29 l were circulated in the column set loop, formed with all columns, at a flow rate of 80 l/h.

After equilibration of the system, the following fractions were drawn from the system: one residual fraction from all columns, one rhamnose-containing fraction from all columns and three fucose-containing fractions from the last column. The result including HPLC analyses for combined fractions are set forth in the table below.

| | Fucose | Rhamnose | Residual |
|---|---|---|---|
| Volume, I | 62.0 | 109.0 | 153.0 |
| Dry solids, g/100 ml | 24.9 | 11.1 | 1.7 |
| Fucose, % on DS | 10.9 | 0.5 | 1.5 |
| Rhamnose, % on DS | 7.2 | 37.1 | 11.7 |
| MAX, % on DS | 26.3 | 1.2 | 0.0 |
| Xylose, % on DS | 1.6 | 3.0 | 1.3 |
| Others, % on DS | 54.0 | 58.2 | 85.5 |

The overall yield calculated from the product fractions is 94.4% for fucose and 76% for rhamnose.

It will be obvious to a person skilled in the art that, as the technology advances, the inventive concept can be implemented in various ways. The invention and its embodiments are not limited to the examples described above but may vary within the scope of the claims.

The invention claimed is:

1. A process of recovering fucose from a solution of a hydrolyzate of hemicellulose-containing biomass comprising deoxysugars and other monosaccharides, characterized by subjecting said solution to a process comprising the following steps:

(1) at least one chromatographic fractionation using a column packing material selected from weakly acid cation exchange resins and weakly basic anion exchange resins, and (2) at least one chromatographic fractionation using a column packing material selected from strongly basic anion exchange resins and strongly acid cation exchange resins, and recovering from fractionations (1) and (2) one or more fractions enriched in fucose.

2. A process as claimed in claim 1, characterized by subjecting said solution to two or more of steps (1) and (2).

3. A process as claimed in claim 1, characterized by subjecting said solution two or more times to steps selected from steps (1) and (2).

4. A process as claimed in claim 1, characterized in that the process further comprises recovering a fraction enriched in rhamnose from one of steps (1) and (2).

5. A process as claimed in claim 4, characterized in that said rhamnose is L-rhamnose.

6. A process as claimed in claim 1, characterized in that the process comprises recovering a fraction enriched in fucose from step (2) comprising chromatographic fractionation using a column packing material selected from strongly acid cation exchange resins.

7. A process as claimed in claim 1, characterized in that the process comprises recovering a fraction enriched in rhamnose and a fraction enriched in fucose in one of steps (1) and (2).

8. A process as claimed in claim 1, characterized in that the process comprises recovering a fraction enriched in fucose from step (2) comprising chromatographic fractionation using a column packing material selected from strongly basic anion exchange resins.

9. A process as claimed in claim 1, characterized in that the process comprises the following sequential steps:

(1) subjecting said solution to chromatographic fractionation using a column packing material selected from strongly acid cation exchange resins and recovering a fraction enriched in rhamnose and/or one or more fractions containing fucose, (2) subjecting said one or more fractions containing fucose to chromatographic fractionation using a column packing material selected from weakly acid cation exchange resins and recovering a fraction containing fucose, (3) subjecting said fraction containing fucose to chromatographic fractionation using a column packing material selected from strongly basic anion exchange resins and recovering a fraction enriched in fucose.

10. A process as claimed in claim 1, characterized in that said strongly acid cation exchange resin is in $Na^+$ form.

11. A process as claimed in claim 1, characterized in that said strongly acid cation exchange resin is in $Zn^{+2}$ form.

12. A process as claimed in claim 1, characterized in that said weakly acid cation exchange resin is in $Na^+$ form.

13. A process as claimed in claim 1, characterized in that said strongly basic anion exchange resin is in $HSO_3^-$ form.

14. A process as claimed in claim 1, characterized in that said solution is a solution of a hydrolyzate of hemicellulose-containing plant-based biomass.

15. A process as claimed in claim 14, characterized in that said hydrolyzate of hemicellulose-containing plant-based biomass is a spent liquor obtained from a pulping process.

16. A process as claimed in claim 15, characterized in that said spent liquor has been obtained from hardwood pulping.

17. A process as claimed in claim 14, characterized in that said hydrolyzate of hemicellulose-containing plant-based biomass is selected from a sugar beet-derived solution and a sugar cane-derived solution.

18. A process as claimed in claim 1, characterized in that said process further comprises subjecting said one or more fractions enriched in fucose to crystallization.

19. A process as claimed in claim 18, characterized in that said crystallization is carried out using evaporation and cooling crystallization.

20. A process as claimed in claim 18, characterized in that fucose is crystallized from a solvent selected from water, an alcohol, and a mixture of water and an alcohol.

21. A process as claimed in claim 18, characterized in that the crystallization solvent is water.

22. A process as claimed in claim 20, characterized in that said alcohol is ethanol.

23. A process as claimed in claim 18, characterized in that the crystallization of fucose is carried out from a solution containing more than 45% fucose on DS.

24. A process as claimed in claim 23, characterized in that the crystallization of fucose is carried out from a solution containing more than 80% fucose on DS.

25. A process as claimed in claim 23, characterized in that the crystallization of fucose is carried out from a solution containing less than 20% rhamnose, less than 15% xylose, less than 3% arabinose and less than 1% galactose on DS.

26. A process as claimed in claim 23, characterized in that the crystallization of fucose is carried out from a solution containing more than 45% fucose, less than 20% rhamnose, less than 15% xylose, less than 3% arabinose and less than 1% galactose on DS.

27. A process as claimed in claim 18, characterized in that the crystallization of fucose is carried out by fractional crystallization.

28. A process as claimed in claim 27, characterized in that the process provides crystalline fucose with a purity of more than 60% on DS.

29. A process as claimed in claim 27, characterized in that fucose has a purity of more than 90% on DS.

30. A process as claimed in claim 27, characterized in that fucose has a purity of more than 99% on DS.

31. A process as claimed in claim 1, characterized in that said fucose is L-fucose.

32. A process for the crystallization of fucose, characterized in that the crystallization of fucose is carried out from a solution of a hydrolyzate of hemicellulose-containing biomass, which contains more than 45% fucose, less than 20% rhamnose, less than 15% xylose, less than 3% arabinose and less than 1% galactose.

33. A process for the crystallization of fucose, characterized in that the crystallization of fucose is carried out from a solution of a hydrolyzate of hemicellulose-containing biomass, which contains more than 80% fucose, less than 20% rhamnose, less than 15% xylose, less than 3% arabinose and less than 1% galactose on DS.

34. A process as claimed in claim 33, characterized in that the crystallization of fucose is carried out in a temperature range of 0 to 100° C.

35. A process as claimed in claim 33, characterized in that the crystallization of fucose is carried out with a residence time of 6 to 80 hours.

36. A process as claimed in claim 18, 32 or 33, characterized in that the process comprises washing the crystals obtained from the crystallization.

37. A process as claimed in claim 36, characterized in that the washing agent is selected from water, an organic solvent or a mixture thereof.

38. A process as claimed in claim 26 or 32, characterized in that said crystallization is carried out at a temperature range of 0 to 100° C.

39. A process as claimed in claim 26 or 32, characterized in that the viscosity of the resulting crystallization mass is in the range of 5 to 500 Pas.

40. A process as claimed in claim 26 or 32, characterized in that the crystallization is carried out using a mixture of water and ethanol as the solvent.

41. A process as claimed in claim 26 or 32, characterized in that the crystallization is carried out with a residence time of 0.5 to 10 days.

42. A process for the crystallization of fucose, characterized in that the crystallization of fucose is carried out from a solution of a hydrolyzate of hemicellulose-containing biomass, which contains more than 80% fucose, less than 20% rhamnose, less than 15% xylose, less than 3% arabinose and less than 1% galactose on DS and the crystallization provides crystalline fucose having a purity of more than 99% on DS.

43. Crystalline L-fucose based on biomass, characterized in that it has a melting point higher than 141° C. measured by the European Pharmacopeia method and a purity higher than 99% on DS.

44. Crystalline L-fucose as claimed in claim 43, characterized in that it has a melting point higher than 145° C.

45. Crystalline L-fucose as claimed in claim 43, characterized in that it has a melting point higher than 142° C.

46. Crystalline L-fucose as claimed in claim 43, characterized in that it has a melting point higher than 142.5° C.

47. Crystalline L-fucose as claimed in claim 43, characterized in that it is based on plant biomass.

48. Crystalline L-fucose based on plant biomass, characterized in that it has a melting point higher than 145° C. measured by the European Pharmacopeia method and a purity higher than 99% on DS.

* * * * *

UNITED STATES PATENT AND TRADEMARK OFFICE

CERTIFICATE OF CORRECTION

PATENT NO. : 7,037,378 B2 
APPLICATION NO. : 10/670094
DATED : May 2, 2006
INVENTOR(S) : Juho Jumppanen et al.

It is certified that error appears in the above-identified patent and that said Letters Patent is hereby corrected as shown below:

On the title page, item [73] Assignee:

"Danisco Sweetners" should read as --Danisco Sweeteners--

Signed and Sealed this

Thirteenth Day of March, 2007

JON W. DUDAS
*Director of the United States Patent and Trademark Office*